United States Patent [19]

Yamashita

[11] Patent Number: 4,746,469
[45] Date of Patent: May 24, 1988

[54] METHOD FOR PREPARING PLATED DENTURES

[75] Inventor: Atsushi Yamashita, Okayama, Japan

[73] Assignee: G-C Dental Industrial Corp., Tokyo, Japan

[21] Appl. No.: 924,761

[22] Filed: Oct. 30, 1986

[30] Foreign Application Priority Data

Nov. 15, 1985 [JP] Japan .................. 60-255116

[51] Int. Cl.⁴ .......................................... A61C 13/10
[52] U.S. Cl. ........................................ 264/18; 264/22; 264/271.1; 264/17; 433/214; 433/37
[58] Field of Search ................ 264/16, 17, 18, 22, 264/25; 433/167, 171, 199.1, 214, 37

[56] References Cited

U.S. PATENT DOCUMENTS

| | | | |
|---|---|---|---|
| 3,421,501 | 1/1969 | Beightol | 264/22 |
| 3,460,252 | 8/1969 | Schneider et al. | 433/171 |
| 3,621,575 | 11/1971 | Schneider et al. | 433/171 |
| 4,012,838 | 3/1977 | Abdenour | 433/171 |
| 4,267,133 | 5/1981 | Kohmura et al. | 264/18 |
| 4,439,380 | 3/1984 | Michl et al. | 264/22 |
| 4,457,713 | 7/1984 | Schneider | 433/171 |
| 4,521,193 | 6/1985 | Cialone | 264/18 |

FOREIGN PATENT DOCUMENTS

| | | | |
|---|---|---|---|
| 4641117 | 4/1968 | Japan | 264/22 |
| 0106953 | 6/1984 | Japan | 264/22 |

*Primary Examiner*—Richard V. Fisher
*Assistant Examiner*—Coreen Y. Lee
*Attorney, Agent, or Firm*—Oblon, Fisher, Spivak, McClelland & Maier

[57] ABSTRACT

A method for directly preparing a plated denture having improved accuracy within a short period of time by properly using photo-polymerizable resins having varied viscosities, and using as the impression material a dough product of photo-polymerizable resins having different viscosities with preparing of a basic plate, formation of alveolar ridge portion, arrangement of artificial teeth, formation of gingival portion, whereby the impression of the details of the mucosal surface of the oral mouth is reproduced with high fidelity, and is then polymerized and cured as such by active energy beams to use it as the resin surface.

1 Claim, 2 Drawing Sheets

METHOD FOR PREPARING PLATED DENTURES

BACKGROUND OF THE INVENTION

1. Field of the Invention

The present invention relates to a method for preparing a partial or a full plated denture for the upper and the lower jaws by the direct impression method having improved accuracy within a short period of time in an economical manner, using photo-polymerizable resins.

2. Prior Art

Heretofore, the preparation of plated dentures has relied upon the indirect methods, and has required a number of stages. In the prior art, a great deal of time and labor have been required to obtain finished plated dentures, and specific instruments have been used in the respective steps. For instance, the steps required to prepare plated dentures with the use of thermal-polymerizable resin systems involve a number of processes such as preliminary impression taking; preparation of models; preparation of individual impression trays; trying-in of individual impression trays in the oral mouth; functional impression taking and muscle plasty; preparation of working models; correction of working models; preparation of bite plates; bite taking; attachment of articulators; arrangement of artificial teeth; trying-in and adjustment of wax dentures in the oral mouth; formation of gingival portion; investment of wax dentures; wax washing out; application of resin separators; resin doughing; resin filling; thermal-polymerization of resins; removal of polymerized dentures; and polishing. Thus, it generally takes a period of about four to six weeks for the patient to give access to the finished plated denture, during which a considerable amount of labor and a great number of the instruments used in the respective steps are required.

Attempts have been made to reduce an extended period of time, a great deal of labor and a large number of instruments applied in the respective steps, which are caused by a large number of the steps for preparing plated dentures. Japanese Patent Laid-Open Publication No. 60-90552 teaches among others, use of a photo-polymerizable resin, and Japanese Patent Publication No. 46-24868 as well as U.S. Pat. Nos. 3,460,252 and 3,621,575 teach use of self curing resins. In these specifications, the photo-polymerizable and self curing resins are used in place of the thermal-polymerizable resin to substitute them for wax dentures in the steps of preparing plated dentures of the thermal-polmerizable resin system, whereby it is possible to omit some of the craftsman's procedures such as investment of wax dentures, wax washing out, application of resin separators, resin doughing, resin filling, removal of polymerized dentures, etc.

The method for preparing plated dentures with the use of thermal-polymerizable resin systems involves a great number of steps and requires a considerably prolonged period and a great deal of labor to obtain finished dentures. Further, considerable types of instruments should be used in the respective steps. For that reason, there is inevitably a rise in the price of finished plated dentures. Still further, the finished plated dentures are not always enhanced in the fitting accuracy in the oral mouth. In other words, noticeable difficulty is encountered in obtaining precise working models, since errors occur in the procedures for reproducing the oral mouth conditions thereon such as, for instance, making of individual impression trays, trying-in of individual impression trays in the oral mouth, functional impression taking, muscle plasty, preparation of working models and correction of working models. Still further, the thermal-polymerizable resin in itself has a large shrinkage upon polymerization of as high as about 9.5%, so that there occur errors such as misalignment of the upper and lower halves of the flask in which the resin is filled when it is replaced for wax dentures, unfitness caused by the thickness of flashes, deformation of gypsum at the time of polymerization, deformation of resin due to rapid heating or cooling, deformation of dentures at the time of removing the dentures from the investing stone, etc. This makes it very difficult to obtain plated dentures with improved fitting accuracy.

On the other hand, the method for preparing plated dentures with photo-polymerizable and self curing resins can be carried out in a smaller number of steps as compared with the method in which the thermal-polymerizable resin is used, since the steps of replacing resin for wax dentures can be omitted. However, that method still requires a considerably number of steps and a great deal of time to be consumed by the time the plated dentures are completed, during which a great deal of labor is also needed. In addition, the instruments used in the respective steps are considerably large in type and number. For such reasons as mentioned just above, the price of the finished plated dentures is none too low. In view of the fitting accuracy of the finished plated dentures in the oral mouth, the aforesaid method is still unsatisfactory. In other words, the method for preparing plated dentures with the photo-polymerizable resin and self curing resin still requires the step of reproducing the oral mouth conditions on working models, during which errors are apt to be left as they are. Referring to the photo-polymerizable resin, only one type of a photo-polymerizable resin having a high viscosity should be used, so that difficulty is encountered in obtaining plated dentures with improved fitting accuracy, since the details of the surface of gypsum models are only reproduced with poor fidelity. When the self curing resin is used, curing begins to take place at a very early stage, so that manipulation is very troublesome. It is thus very difficult to obtain plated dentures with satisfactory fitting accuracy.

SUMMARY OF THE INVENTION

An object of the present invention is to provide a method for preparing plated dentures, which makes it possible to reduce the number of the steps involved, shorten the time required for the completion of plated dentures, diminish the amount of labor consumed in the preparation steps, reduce the types of instruments used in the preparation steps, cut down the price of plated dentures and improve the fitting accuracy of plated dentures in the oral mouth.

As a result of extensive and intensive studies made for the purpose of achieving the foregoing and other objects, it has been found that, according to the present invention, plated dentures with improved direct accuracy can be obtained within a short period of time by properly using photo-polymerizable resins having varied viscosities, and using as the impression material a dough product of photo-polymerizable resins having different viscosities simultaneously with provision of a basic plate, formation of alveolar ridge portion, arrangement of artificial teeth formation of gingival portion, whereby the impression of the details of the mucosal surface of the oral mouth is polymerized and cured as such to use it as the resin surface.

Thus the present invention enables to get a plated denture with rich fidelity within a short period of time.

BRIEF DESCRIPTION OF THE DRAWINGS

In the following, the method for preparing plated dentures according to the present invention will now be explained with reference to FIGS. 1 to 11, which are given for the purpose of illustration alone, and in which.

PREFERRED EMBODIMENTS OF THE INVENTION

Figure 1:
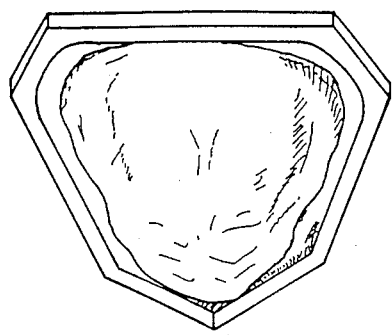
FIG. 1 is a perspective view showing a gypsum model prepared on the basis of an impression formed of an alginate impression material.
Figure 2:
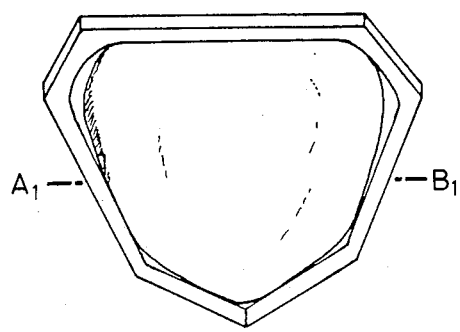
FIG. 2 is a perspective view showing a basic plate on the gypsum model, which is composed of a photo-polymerizable resin having a relatively high viscosity.
Figure 3:
FIG. 3 is an end view of the basic plate taken along the line $A_1$–$B_1$ of FIG. 2.
Figure 4:
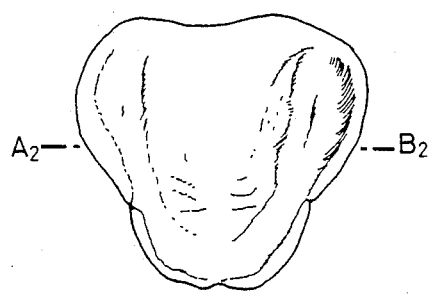
FIG. 4 is a perspective view showing a plate including a corrected impression formed of a photo-polymerizable resin having a lower viscosity.
Figure 5:
FIG. 5 is an end view taken along the line $A_2$–$B_2$ of FIG. 4.
Figure 6:
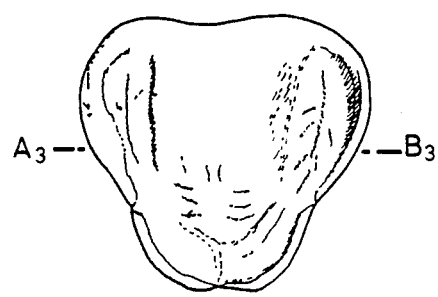
FIG. 6 is a perspective view showing a plate including a functional impression formed of a photo-polymerizable resin having a much lower viscosity.
Figure 7:
FIG. 7 is an end view taken along the line $A_3$–$B_3$ of FIG. 6.
Figure 8:
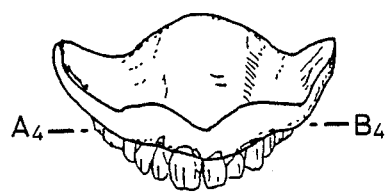
FIG. 8 is a perspective view showing a plate to which formation of alveolar ridge portion, arrangement of artificial teeth are applied with a photo-polymerizable resin having a relatively high viscosity.
Figure 9:
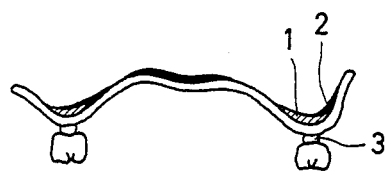
FIG. 9 is an end view taken along the line $A_4$–$B_4$ of FIG. 8.
Figure 10:
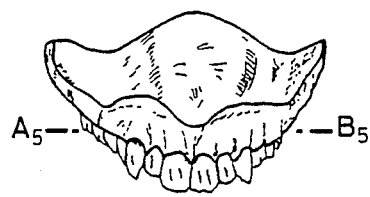
FIG. 10 is a perspective view showing a plate including a gingival portion formed of a photo-polymerizable resin having a medium viscosity.
Figure 11:
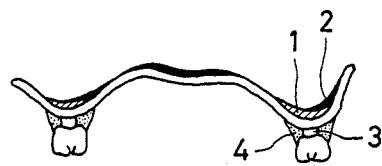
FIG. 11 is an end view taken along the line $A_5$–$B_5$ of FIG. 10.

After a preliminary impression has been taken, a gypsum model as illustrated in FIG. 1 is first prepared. A photo-polymerizable resin having a relatively high viscosity is allowed to be in pressure contact with the gypsum model, and is polymerized and cured by irradiation of active energy beams to prepare a basic plate as shown in FIGS. 2 and 3. Subsequently, a photo-polymerizable resin having a lower viscosity which is lower than that of said basic plate-forming resin is applied on the inner face of the basic plate. After a corrected impression has been taken, it is exposed to active energy beams to form a plate as shown in FIGS. 4 and 5. Thereupon, a photo-polymerizable resin having a much lower viscosity is applied on the inner face of the plate including the corrected impression to take a functional impression. It is then exposed to active energy beams to obtain a plate including the functional impression, as shown in FIGS. 6 and 7. According to the known methods, thereafter, formation of a bite plate, bite taking and attachment of an articulator are carried out. Following the occlusal plane reproduced on the articulator, artificial teeth are then arranged on formation of alveolar ridge portion on the outside of the aforesaid plate including the functional impression, using a photo-polymerizable resin having a relatively high viscosity. After fine occlusal equilibration, active energy beams are applied to make an artificial teeth-arranged plate, as shown in FIGS. 8 and 9. Thereafter, a photo-polymerizable resin having a medium viscosity is applied into the gingival portion of said aritificial teeth-arranged plate, which is in turn exposed to active energy beams to form a plated denture, as shown in FIGS. 10 and 11.

Briefly, varied photo-polymerizable resins having varied viscosities are properly used in the method for preparing plated dentures according to the present invention. More specifically, according to the present invention, plated dentures with improved accuracy can be prepared within a short period of time by providing a basic plate formed of a photo-polymerizable resin having a relatively high viscosity, and formation alveolar ridge portion, arrangement of artificial teeth, formation of gingival portion on the outside thereof with photo-polymerizable resins having a relatively high viscosity and a medium viscosity, while using as the impression materials with photo-polymerizable resins having a lower viscosity and a much lower viscosity to directly take the impression of the details of the oral mouth mucosal by the corrected and functional impressions, said impression materials being photo-polymerized and cured as such to use them as the resin surface. Especially when the impression of the details of the mucosal surface of the oral mouth is taken, the fluidable photo-polymerizable resins having a lower viscosity and a much lower viscosity are used to repeat corrected impression taking and functional impression taking, whereby the impression of the oral mouth can be impressed with high accuracy but without exerting any pressure upon the soft and elastic oral mouth mucosal and alveolar surface, so that the fitting accuracy of the plated dentures is further improved. In addition, since the finished plated dentures are of the structure that the photo-polymerized resins having uniform strength are superposed one upon another, after photo-polymerization, they can stand up to fatigue due to repeated bending or impact, and thus excel in durability.

The photo-polymerizable resins having varied viscosities may properly be colored for discrimination. Such color discrimination makes it advantageously possible to pass judgement on how lamination is effected on what steps.

According to the invented method for preparing plated dentures, it is possible to directly prepare plated dentures without reproducing the oral mouth conditions on a working model. Consequently, it is possible to omit certain steps needed in the conventional indirect method for preparing plated dentures with the thermal-polymerizable resin such as, for instance, reproduction of the oral mouth conditions on working models which involves preparation of individual impression trays, trying-in of the individual impression trays in the oral mouth, functional impression taking and muscle plasty, preparation of working models and correction of working models; replacement of resin for wax dentures which involves investment of wax dentures, wax washing out, application of resin separators, doughing of thermal-polymerizable resins, filling of thermal-polymerizable resins, polymerization of thermal-polymerizable resin and removal of plated dentures, and the like. Consequently, it is possible to considerably reduce the number of steps required for the preparation of plated dentures, the time consumed for the completion of plated dentures, the amount of labor consumed in the respective steps and the types of instruments used in the respective steps; this means that plated dentures with high accuracy can economically be prepared within a short period of time.

The photo-polymerizable resins having a relatively high viscosity, a medium viscosity, a lower viscosity and a much lower viscosity used in the present invention comprise a polymerizable ethylenical compound containing at least one ethylenically unsaturated double-bond, a photo-polymerization initiator, a photo-sensitizer and a filler, are different from one another in the viscosity alone, and are capable of being polymerized and cured by active energy beams.

The ethylenical compounds used in the present invention refer to those having in their chemical structure at least one ethylenically unsaturated double-bond and taking on the chemical form of monomers, prepolymers (viz., dimers, trimers and other oligomers) or mixtures and copolymers thereof.

Concretely, the monomers having therein one ethylenically unsaturated double-bond include methyl, ethyl, isopropyl, hydroxyethyl, tetrahydrofurfuryl and glycidyl acrylates and methacrylates thereof. The aromatic monomers having therein two ethylenically unsaturated double-bonds include 2,2-bis(methacryloxyphenyl)propane, 2,2-bis[4-(2-hydroxy-3-methacryloxyphenyl)]propane, 2,2-bis(4-methacryloxyethoxyphenyl)propane, 2,2-bis(4-methacryloxydiethoxyphenyl)propane, 2,2-bis(4-methacryloxypropoxyphenyl)propane, and acrylates thereof, and the aliphatic monomers having therein two ethylenically unsaturated double-bonds include ethylene glycol, diethylene glycol, triethylene glycol, butylene glycol, neopentyl glycol, polypropylene glycol, 1,3-butanediol, 1,4-butanediol and 1,6-hexanediol dimethacrylates and diacrylates thereof. The monomers having therein three ethylenically unsaturated double-bonds include trimethylolpropane, trimethylolethane, pentaerythritol and trimethylolmethane trimethacrylates and triacrylates thereof. The monomers having therein four ethylenically unsaturated double-bonds include pentaerythritol tetramethacrylate and pentaerythritol tetracrylate as well as urethane base monomers such as urethane diacrylate and dimethacrylate.

As the photo-polymerizable initiators, use may be made of benzoin, benzoin alkyl ethers, benzophenone, acetophenone and their derivatives, thioxantone and its derivatives, benzyl, camphor quinone, α-naphtyl, acenaphthene, p,p'-dimethoxybenzyl, p,p'-dichlorobenzyl, etc. As the photosensitizers, use may be made of dimethylaminoethyl methacrylate, n-butylamine, triethylamine, triethyl-n-butylphosphine, 4-dimethylaminobenzoic acid isoamyl ester, etc.

The fillers used may be inorganic and/or organic ones. For instance, use may be made of powdered quartz, powdered alumina, powdered glass, kaolin, talc, calcium carbonate, barium aluminosilicate glass, titanium oxide, borosilicate glass, powdered colloidal silica and the so called organic composite filler in which an inorganic filler of colloidal silica is coated with an organic polymer, and the powders of polymers such as polymethyl acrylate, polymethyl methacrylate, polyethyl methacrylate, copolymers of methyl methacrylate with ethyl methacrylate, crosslinked type polymethyl methacrylate and copolymers of ethylene with vinyl acetate. These polymer powders may be used in the form of mixtures with the aforesaid inorganic powders.

It is preferred that, prior to mixing the inorganic filler with the binder resin, that filler is treated on its surface with a coupling agent capable of reacting with both the filler and the binder resin.

The coupling agents use may include a silane coupling agent, a titanate coupling agent, an aluminate coupling agent and the like. Alternatively, the inorganic filler may be grafted on the surface for bonding to the binder resin.

The silane coupling agent used to this end include γ-methacryloxypropyl trimethoxysilane, vinyltrichlorosilane, vinyl-tris(β-methoxyethoxy)silane, γ-methacryloxypropylmethyl dimethoxysilane, γ-glycidoxypropyl trimethoxysilane, γ-chloropropyl trimethoxysilane, β-(3,4-epoxycyclohexyl)ethyl trimethoxysilane, trimethylchlorosilane, dimethyldichlorosilane, hexamethyldisilane, γ-aminopropyl triethoxysilane, N-β-(aminoethoxy)-γ-aminpropyl trimethoxysilane, γ-urenoidopropyl trimethoxysilane and the like.

In the present invention, any method for the surface treatment with these coupling agents may be used. The amount of said surface treatment agents used varies depending upon the nature and state required, and is not generally determind. Generally, however, said surface treatment agents may be used in an amount ranging from 0.1 to 20 weight %, preferably 1 to 10 weight %.

The active energy beams used in the present invention may be visible rays or ultraviolet rays, or may contain in their spectra both visible and ultraviolet rays. A preferred wavelength ranges from 240 nm to 600 nm. The light sources applicable to the method of the present invention include carbon arc, mercury lamps, xenon lamps, metal halide lamps, fluorescent lamps, tungsten lamps, argon ion laser and the like.

The present invention will now be concretely explained with reference to examples, but it is understood that the invention is not exclusively restricted thereto.

EXAMPLE 1

In Example 1, the photo-polymerizable resins having a relatively high viscosity, a medium viscosity, a lower viscosity and a much lower viscosity had the following compositions.

| COMPOSITION | parts by weight |
|---|---|
| PHOTO-POLYMERIZABLE RESIN HAVING A RELATIVELY HIGH VISCOSITY | |
| 2,2-bis[4-(2-hydroxy-3-methacryloxyphenyl)]propane | 70 |
| triethylene glycol dimethacrylate | 30 |
| benzophenone | 1 |
| dimethylaminoethyl methacrylate | 0.5 |
| finely powdered silica | 100 |
| PHOTO-POLYMERIZABLE RESIN HAVING A MEDIUM VISCOSITY | |
| 2,2-bis[4-(2-hydroxy-3-methacryloxyphenyl)]propane | 70 |
| ethylene glycol dimethacrylate | 30 |
| benzophenone | 1 |
| dimethylaminoethyl methacrylate | 0.5 |
| finely powdered silica | 80 |
| PHOTO-POLYMERIZABLE RESIN HAVING A LOWER VISCOSITY | |
| 2,2-bis[4-(2-hydroxy-3-methacryloxyphenyl)]propane | 70 |
| ethylene glycol dimethacrylate | 30 |
| benzophenone | 1 |
| dimethylaminoethyl methacrylate | 0.5 |
| finely powdered silica | 30 |
| polymethyl methacrylate | 10 |
| PHOTO-POLYMERIZABLE RESIN HAVING A MUCH LOWER VISCOSITY | |
| 2,2-bis[4-(2-hydroxy-3-methacryloxyphenyl)]propane | 70 |
| triethylene glycol dimethacrylate | 30 |
| benzophenone | 1 |

| COMPOSITION | parts by weight |
|---|---|
| dimethylaminoethyl methacrylate | 0.5 |
| finely powdered silica | 15 |
| polymethyl methacrylate | 10 |

With the aforesaid four photo-polymerizable resins, a plated denture was prepared according to the following steps.

1. An oral impression was taken with an alginate impression material.
2. A gypsum slurry (the gypsum manufactured under the trade name of Fujilock, by G-C Dental Industrial Corp., which mixed with water in the standard proportion) was poured into the impression to prepare a gypsum model as shown in FIG. 1.
3. The photo-polymerizable resin having a relatively high viscosity was allowed to come into pressure contact with the gypsum model, and was exposed to ultraviolet rays emanating from an equipment (manufactured under the trade name of Permacure-UC-1 by G-C Dental Equipment Corp.) to polymerize and cure the resin and thereby prepare a basic plate as shown in FIG. 2.
4. The photo-polymerizable resin having a lower viscosity was applied on the basic plate to take a corrected impression, which was in turn exposed to ultraviolet rays to polymerize and cure the resin (shown at 1 in FIG. 5) and thereby prepare a plate having the corrected impression.
5. The photo-polymerizable resin having a much lower viscosity was applied on the inner face of the plate having the corrected impression to take a functional impression, which was then exposed to ultraviolet rays to polymerize and cure the resin (shown at 2 in FIG. 7).
6. The photo-polymerizable resin having a relatively high viscosity was applied on the plate having the functional impression to form a alverolar ridge to arrange an artificial teeth following the occlusal plane, and was then irradiated with ultraviolet rays for polymerization and curing thereof (as shown at 3 in FIG. 9).
7. The photo-polymerizable resin having a medium viscosity was used to form a gingival portion, which was in turn irradiated with ultraviolet rays for the polymerization and curing thereof (as shown at 4 in FIG. 11).

In this manner, the plated denture was prepared.

EXAMPLE 2

In Example 2, the photo-polymerizable resins having a relatively high viscosity, a medium viscosity, a lower viscosity and a much lower viscosity had the following compositions.

| COMPOSITION | parts by weight |
|---|---|
| PHOTO-POLYMERIZABLE RESIN HAVING A RELATIVELY HIGH VISCOSITY | |
| urethane dimethacrylate | 70 |
| butanediol dimethacrylate | 30 |
| camphor quinone | 0.5 |
| triethanolamine | 0.5 |
| powdered silica treated with γ-methacryloxypropyl trimethoxysilane | 100 |
| PHOTO-POLYMERIZABLE RESIN HAVING A MEDIUM VISCOSITY | |
| urethane dimethacrylate | 70 |
| butanediol dimethacrylate | 30 |
| camphor quinone | 0.5 |
| triethanolamine | 0.5 |
| powdered silica treated with γ-methacryloxypropyl trimethoxysilane | 80 |
| PHOTO-POLYMERIZABLE RESIN HAVING A LOWER VISCOSITY | |
| urethane dimethacrylate | 70 |
| butanediol dimethacrylate | 30 |
| camphor quinone | 0.5 |
| triethanolamine | 0.5 |
| powdered silica treated with γ-methacryloxypropyl trimethoxysilane | 30 |
| polymethyl methacrylate | 10 |
| PHOTO-POLYMERIZABLE RESIN HAVING A MUCH LOWER VISCOSITY | |
| urethane dimethacrylate | 70 |
| butanediol dimethacrylate | 30 |
| camphor quinone | 0.5 |
| triethanolamine | 0.5 |
| powdered silica treated with γ-methacryloxypropyl trimethoxysilane | 20 |
| polymethyl methacrylate | 10 |

To prepare a plated denture from the aforesaid four resins, the procedures of Example 1 were repeated, except that visible rays (with a wavelength of 400 nm) were used as the active energy beams.

COMPARISON EXAMPLE 1

A plated denture was prepared from the thermal-polymerizable resins according to the following steps.

1. A preliminary oral impression was taken with an alginate impression material.
2. A gypsum slurry was poured into the impression to prepare a gypsum model.
3. A self curing resin (manufactured under the trade name of Ostlon by G-C Dental Industrial Corp.) was allowed to come into pressure contact with the gypsum model to prepare an individual impression tray.
4. The individual impression tray was tried in the oral mouth, and was adjusted by means of a stamp bar.
5. A rubber base impression material (manufactured under the trade name of Surflex F by G-C Dental Industrial Corp.) was applied on the impression face side of the individual impression tray to take a functional impression.
6. The impression tray having said functional impression was boxed therearound with a wax, and a gypsum slurry was poured in the box to prepare a working model.
7. The working model was regulated with a model trimmer.
8. With a paraffin wax, a bite plate was prepared on the working model.
9. The bite plate was tried in the oral mouth for bite taking.
10. The working model and the bite plate were attached to an articulator.
11. Artificial teeth were arranged on the bite plate on the articulator to prepare a wax denture.
12. The wax denture was tried in the oral mouth for regulation.
13. A was was applied on the gingival portion of the wax denture for gingivoplasty.
14. The wax denture was placed in a flask, and was invested into an investing gypsum (manufactured under the trade name of Advastone by G-C Dental Industrial Corp.).

15. The wax denture invested in the gypsum was washed out in a wax washing out tank.
16. A resin separator was applied on the gypsum surface.
17. A thermal-polymerizable resin (manufactured under the trade name of Acron by G-C Dental Industrial Corp.) was subjected to powder/liquid mixing for doughing.
18. The doughed, thermal-polymerizable resin was filled in the space in which the wax denture was washed out.
19. The invested gypsum having therein the thermal-polymerizable resin was set in a thermal polymerization device for thermal-polymerization.
20. The polymerized resin was taken out of the gypsum.
21. Gypsum deposited onto the polymerized resin denture was removed with the use of an electrical engine.

COMPARISON EXAMPLE 2

With the photo-polymerizable resin having a relatively high viscosity described in Example 2, a plated denture was prepared by the following steps.

1. A working model was prepared by the steps 1 to 7 described in Comparison Example 1.
2. The photo-polymerizable resin having a relative high viscosity was allowed to come into pressure contact with the working model, and was exposed to ultraviolet rays (having a wavelength of 400 nm) to polymerize and cure it, thereby preparing an individual impression tray.
3. With silicone putty (manufactured under the trade name of Exaflex HB Type by G-C Dental Industrial Corp.), an alveolar ridge was formed on the individual impression tray to prepare an individual impression tray having an alveolar ridge.
4. After bite taking had been carried out with the plate having an alveolar ridge, it was attached to an articulator to reproduce an occlusal plane on the articulator.
5. With the photo-polymerizable resin having a relatively high viscosity, artificial teeth were arranged following the occlusal plane, and the resin was irradiated with visible rays for the polymerization and curing.
6. With the photo-polymerizable resin having a relatively high viscosity, a gingival portion was formed, and the resin was again irradiated with visible rays for the polymerization and curing.

Plated dentures for the same patient were prepared according to the procedures of Examples 1 and 2 as well as Comparison Examples 1 and 2. Thereafter, silicone base materials for fitting testing (manufactured under the trade name of Fit Checker by G-C Dental Industrial Corp.) were applied on the mucosal surfaces of the respective plated dentures to determine their fitting accuracy in terms of the amount of said materials deposited and remaining thereon. The results are set forth in the following table.

TABLE

| | Testing Result | |
|---|---|---|
| | Amount of Testing Material Deposited | Fitting Accuracy |
| Example 1 | Extremely Small | Satisfactory |
| Example 2 | Extremely Small | Satisfactory |
| Comparison Example 1 | Considerably Large | Unsatisfactory |
| Comparison Example 2 | Somewhat Large | Somewhat Unsatisfactory |

According to the invented method for preparing plated dentures, as described in Examples 1 and 2, it was possible to omit some steps needed in the conventional plated denture-preparing methods using a thermal-polymerizable resin (Comparison Example 1) and a photo-polymerizable resin (Comparison Example 2) such as, for instance, reproduction of the oral mouth conditions on working models which involves preparation of individual impression trays, trying-in of the individual impression trays in the oral mouth, functional impression taking and muscle plasty, preparation of working models and correction of working models and the like. It was further possible to omit the works for replacement of resin for wax dentures which are needed in the method using a thermal-polymerizable resin (Comparison Example 1), and involving investment of wax dentures, wax washing out, application of resin separators, doughing of thermal-polymerizable resins, filling of thermal-polymerizable resins, polymerization of thermal-polymerizable resins, removal of plated dentures and the like.

Accordingly, the number of the steps of preparing plated dentures could considerably be reduced. The time required for the completion of plated dentures could also be largely shortened. Further, the amount of labor consumed for the preparation of plated dentures could considerably be decreased. In addition, it was possible to considerably reduce the types of instruments used in the respective steps. As a result, the price of the finished plated dentures could largely be cut down.

Referring to accuracy, the conventional methods for preparing plated dentures, as described in Comparison Examples 1 and 2, have required the works for reproduction of the oral mouth conditions on working models and replacement of resin for wax dentures, which have been responsible for errors and hence a drop of accuracy. According to the present invention which makes the omission of such works feasible, however, plated dentures with much improved accuracy can be obtained, as will be appreciated from the results set forth in the foregoing table, since the preparation of plated dentures can directly be carried out without reproducing the oral mouth conditions on working models. Especially when the impression of the details of the mucosal surface of the oral mouth is taken, the fluidable photo-polymerizable resins having a lower viscosity and a much lower viscosity are used to repeat corrected impression taking and functional impression taking, whereby the impression of the oral mouth can be impressed with high accuracy but without exerting any pressure upon the soft and elastic alveolar surface and mucosal surface of the oral mouth, so that the fitting accuracy of the plated dentures is further improved.

According to the method of the present invention for preparing plated dentures, considerable improvements are introduced into accuracy, since the plated dentures can directly be prepared by separate use of various photo-polymerizable resins having varied viscosities with no need of reproducing the oral mouth conditions on working models which is required in the conventional indirect methods for preparing plated dentues upon thermal- or photo-polymerizable resins. According to the present invention, the number of steps and period of time needed for the preparation of plated dentures are also considerably reduced. In addition, the amount of labor consumed in the preparation of plated dentures is reduced. In consequence, the price of the finished dentures can be cut down to a noticeable degree.

Due to their structure comprising a stack of the photo-polymerizable resins, the finished dentures can stand up to repeated bending or impact, and thus excel in durability. Taken altogether, the present invention makes it possible for not only operators but also patients to economically obtain highly accurate plated dentures within a very short period of time.

What is claimed is:

1. A method for directly preparing a plated denture with photo-polymerizable resins having varied viscosities, which comprises the steps of:

allowing a photo-polymerizable resin having a relatively high viscosity to come into pressure contact with a gypsum model and, thereafter, polymerizing and curing said resin by irradiation of active energy beams to prepare a basic plate;

applying a photo-polymerizable resin having a lower viscosity which is lower than that of said basic plate resin upon the inner face of said basic plate and taking a corrected impression in the oral mouth and, thereafter, polymerizing and curing said resin by irradiation of active energy beams to form a plate having the corrected impression;

applying a photo-polymerizable resin having a much lower viscosity upon the inner face of said plate having the corrected impression and taking a functional impression in the oral mouth and, thereafter, polymerizing and curing said resin by irradiation of active energy beams;

using a photo-polymerizable resin having a relatively high viscosity to form an alveolar ridge portion on the outside of the thus obtained plate and arranging artificial teeth on said plate and, thereafter, polymerizing and curing said resin by irradiation of active energy beams; and using a photo-polymerizable resin having a medium viscosity to form a gingival portion and, thereafter, polymerizing and curing said resin by irradiation of active energy beams to form a plated denture.

* * * * *